(12) United States Patent
Kaneko et al.

(10) Patent No.: US 10,350,588 B2
(45) Date of Patent: Jul. 16, 2019

(54) CLEAN AIR APPARATUS

(71) Applicant: Hitachi Industrial Equipment Systems Co., Ltd., Chiyoda-ku, Tokyo (JP)

(72) Inventors: Takeshi Kaneko, Tainai (JP); Hirotoshi Sato, Tainai (JP); Yukio Mori, Okazaki (JP); Yukiyasu Sano, Yokohama (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 218 days.

(21) Appl. No.: 15/540,765

(22) PCT Filed: Dec. 22, 2015

(86) PCT No.: PCT/JP2015/085785
§ 371 (c)(1),
(2) Date: Jun. 29, 2017

(87) PCT Pub. No.: WO2016/143228
PCT Pub. Date: Sep. 15, 2016

(65) Prior Publication Data
US 2018/0001315 A1    Jan. 4, 2018

(30) Foreign Application Priority Data
Mar. 10, 2015    (JP) .................................. 2015-046797

(51) Int. Cl.
*F24F 7/00*    (2006.01)
*F24F 11/00*    (2018.01)
(Continued)

(52) U.S. Cl.
CPC    *B01L 1/02* (2013.01); *B01L 1/00* (2013.01); *C12M 37/00* (2013.01); *F24F 3/1607* (2013.01);
(Continued)

(58) Field of Classification Search
CPC ........ B01L 1/02; B01L 1/00; B01L 2200/143; B01L 2300/0627; B01L 2300/12; C12M 37/00; F24F 3/1607
(Continued)

(56) References Cited

U.S. PATENT DOCUMENTS

| 5,522,767 A | * | 6/1996 | Rertsche ................ F24F 3/1607 454/187 |
| 6,632,260 B1 | * | 10/2003 | Siemers ............. B01D 46/0013 454/184 |

(Continued)

FOREIGN PATENT DOCUMENTS

| JP | 62-132550 A | 6/1987 |
| JP | 4-288428 A | 10/1992 |

(Continued)

OTHER PUBLICATIONS

International Search Report (PCT/ISA/210) issued in PCT Application No. PCT/JP2015/085785 dated Feb. 9, 2016 with English translation (5 pages).

(Continued)

*Primary Examiner* — Helena Kosanovic
(74) *Attorney, Agent, or Firm* — Crowell & Moring LLP

(57) ABSTRACT

In a state where an operator performs operation using a safety cabinet while confirming standard operating procedures and sample data, a display device such as a monitor screen provided in the safety cabinet is arranged at a position that is not subject to effects of deterioration due to diffused reflection of light from a fluorescent lamp or sterilization lamp irradiation, and that does not generate resistance in an airflow path, while also protecting the display device from decontamination operation and preventing dirt from being adhered to a portion related to display. Transparent windows are provided on both a portion of a back wall or a side wall of a work space in the safety cabinet and a portion of a rear (Continued)

wall or a side wall of the body of the safety cabinet separated from the back wall or the side wall of the work space by a circulation flow path, which allow the operator to see through both walls, and the display device is placed on an outer side portion of the transparent window provided at the portion of the rear wall or the side wall of the body of the safety cabinet.

13 Claims, 8 Drawing Sheets

(51) Int. Cl.
| | | |
|---|---|---|
| *F24F 13/00* | (2006.01) | |
| *B01L 1/02* | (2006.01) | |
| *B01L 1/00* | (2006.01) | |
| *C12M 1/12* | (2006.01) | |
| *F24F 3/16* | (2006.01) | |

(52) U.S. Cl.
CPC . *B01L 2200/143* (2013.01); *B01L 2300/0627* (2013.01); *B01L 2300/0858* (2013.01); *B01L 2300/12* (2013.01)

(58) Field of Classification Search
USPC .......................................................... 454/57
See application file for complete search history.

(56) References Cited

U.S. PATENT DOCUMENTS

| 2012/0019110 A1 | 1/2012 | Ono et al. |
| 2013/0061567 A1* | 3/2013 | Kawasaki ................ B01L 1/04 55/385.2 |
| 2016/0264921 A1 | 9/2016 | Yoneda |

FOREIGN PATENT DOCUMENTS

| JP | 6-297356 A | 10/1994 |
| JP | 2001-141273 A | 5/2001 |
| JP | 2006-6282 A | 1/2006 |
| JP | 2006-122816 A | 5/2006 |
| JP | 2007-175583 A | 7/2007 |
| JP | 2007-185595 A | 7/2007 |
| JP | 2008-200671 A | 9/2008 |
| JP | 2012-24657 A | 2/2012 |
| JP | 2015-100318 A | 6/2015 |

OTHER PUBLICATIONS

Japanese-language Written Opinion (PCT/ISA/237) issued in PCT Application No. PCT/JP2015/085785 dated Feb. 9, 2016 (6 pages).
Japanese-language Office Action issued in counterpart Japanese Application No. 2015-046797 dated May 8, 2018 (11 pages).

* cited by examiner

CLEAN AIR APPARATUS

TECHNICAL FIELD

The present invention relates to a safety cabinet used as an apparatus configured to prevent accidents from occurring caused by handling of cells, microorganisms and pathogens in a field of regenerative medicine in which cells are cultured, and in industrial fields of clinical/pharmaceutical areas in which pathogens are handled and genetic manipulation is carried out. The relationship between the safety cabinet and a "clean air apparatus" used in the title of the invention will be described later.

BACKGROUND ART

In the field of regenerative medicine in which lost functions are restored or replaced and in a field of cell therapy in which cells are administered to treat or relieve diseases or injuries, a fabrication environment of culture pretreatment process using cells and tissues (hereinafter referred to as "samples") extracted from patients must be realized in a work space having a certain level of cleanliness, such that contamination risks of the samples are reduced, diffusion of samples within the work chamber is prevented, and mutual contamination of different samples is prevented. If animal or other person's cells mix into the sample, the sample will be recognized as a foreign substance within a body of the patient, and the sample will be rejected by immune response and defected.

Moreover, in the fabrication environment of sterilized medicine and biological products, contamination risk of medicine is reduced by performing the fabrication in a work space having a certain level of cleanliness. Further, in a research field handling pathogens and carrying out genetic manipulations, a biohazard countermeasure is taken in which human/environment and biological specimen/pathogens are physically isolated.

One apparatus for providing such space is the safety cabinet ("Class II cabinet for biohazard countermeasure" according to Japanese Industrial Standard (JIS)). In the safety cabinet, air is supplied by an air blowing means, and the air is passed through an HEPA filter serving as an air cleaning means, according to which dust contained in the air is removed before the air is supplied to a predetermined space.

As a background art of the present technical field, for example, Japanese Unexamined Patent Application Publication No. 2006-122816 (Patent Literature 1) discloses "a safety cabinet equipped with a cabinet body (1) having a work space (S) under negative pressure provided therein, wherein the work space (S) is formed between a transparent shutter (3) that can be opened and closed provided on a front side of the cabinet body (1) and a rear wall portion (4) arranged behind the shutter (3), wherein the rear wall portion (4) is provided with a monitor screen (M) displaying information necessary for the operation toward a front direction, and a foot switch (2) is provided on a lower portion outside the cabinet body (1) that allows contents of display of the monitor screen (M) to be operated by foot."

CITATION LIST

Patent Literature

[PTL 1] Japanese Unexamined Patent Application Publication No. 2006-122816

SUMMARY OF INVENTION

Technical Problem

PTL 1 (Japanese Unexamined Patent Application Publication No. 2006-122816) discloses a prior art technique of a configuration in which a monitor screen is disposed on a rear wall portion of a work space within a safety cabinet. Specifically, in a work space formed between an openable/closable transparent shutter disposed on a front side of a cabinet body and a rear wall portion arranged behind the shutter, a monitor screen configured to display necessary information for operation is provided toward a front direction on the rear wall portion.

According to the above-described prior art, there is no consideration on the monitor screen causing a resistance to air flow and disrupting air flow balance since the monitor screen is disposed within the work space or the airflow path. Ensuring air flow balance within the limited space inside the apparatus is an important item in the field of safety cabinets. However, there is no disclosure on a method for ensuring air flow balance in a state where a display device such as a monitor is installed in the apparatus.

Moreover, if the configuration of the prior art technique is adopted in a safety cabinet, if the condition of air flow is changed, a physical isolation performance must be evaluated using a Bacillus subtilis spore, as described in Japanese Industrial Standard JIS) K3800 "Class II cabinet for biohazard countermeasure".

In the work space of the safety cabinet, cells and tissues that must not be diffused to the exterior and pathogens used for studies of infectious disease are handled, such that the work space must be sterilized after operation by wiping the work space using an appropriate disinfectant and irradiating sterilization lamp provided in the safety cabinet. Further, during periodic inspection, maintenance checkup or replacement of the HEPA filter, or in a state where the interior of the cabinet is contaminated by a large amount of pathogens, the whole work space must be sterilized in order to detoxify the contaminant.

Normally, formaldehyde gas is used for the sterilization. In that case, the monitor screen will be covered with sterilization gas, which may become a cause of corrosion or malfunction.

However, according to the configuration of the prior art disclosed in Patent Literature 1, there is no consideration on the cause of corrosion or malfunction.

On the other hand, a germicidal lamp irradiates UV-C waves which are ultraviolet rays having a wavelength region of 240 to 260 nm having sterilizing power, to thereby damage the DNA of the bacteria and perform sterilization. However, the effect of the ultraviolet ray deteriorates resin, and the resin portion of the frame of the monitor screen is deteriorated, and causes generation of dust. Therefore, even if the monitor screen is removed from the safety cabinet to detoxify the monitor screen, it was not possible to perform sterilization processing of the inner portion of the monitor screen, and diffusion of contaminant may be caused if the monitor screen was taken out of the safety cabinet.

In the fabrication environment of medicine, for example, it is not only necessary to manage an amount of floating dust within the space but also to form a clean air blown into the work chamber as a laminar flow flowing in one direction. In other words, there is a need to prevent dust at a certain position within the work chamber from expanding to other positions, but the monitor screen disposed within the work chamber becomes a resistance and turbulence is created in the vicinity thereof. Thereby, the monitor screen causes the air flow to blow up or stagnate, and it is therefore not preferable.

Further, the interior of the work chamber of the safety cabinet is covered with a plate formed of SUS 304 and the like for corrosion protection, and light reflectance within the work chamber is high. Therefore, if the monitor screen is disposed on a back face within the work chamber, light from an illuminating lamp provided on the safety cabinet illuminates the monitor either directly or indirectly, causing a problem that the screen is difficult to see.

The object of the present invention is as described below. In a state where an operator performs operation using a safety cabinet while confirming a standard operating procedure manual (hereinafter referred to as "SOP (Standard Operating Procedures)", patient data, type of pathogens, formulation quantity of drug and other data of the samples (hereinafter referred to as "sample data"), a configuration is realized in which a display means such as a monitor screen disposed on the safety cabinet is arranged at a position where the display means does not cause resistance in the airflow path. Further, workability of the operator operating within the work space is improved.

Solution to Problem

A most major characteristics of the present invention is that transparent windows are provided at a portion of a back wall or a side wall of a work space of a safety cabinet and a portion of a rear wall or a side wall of a body separated by a circulation flow path from the back wall or the side wall mentioned above, such that the operator can see through both walls, and in addition, a major characteristics of the present invention is that a display means is disposed on an outer side portion of the transparent window provided at a portion of the rear wall or the side wall of the body of the safety cabinet.

Advantageous Effects of Invention

According to the present invention, a method can be provided in which the operator performing operation in a clean space within the safety cabinet can recognize information outside the work space while ensuring an airflow path within the safety cabinet.

DESCRIPTION OF EMBODIMENTS

Now, first to fifth embodiments as embodiments of the present invention will be described sequentially with reference to FIGS. 1 through 13.

[First Embodiment]

Figure 1:
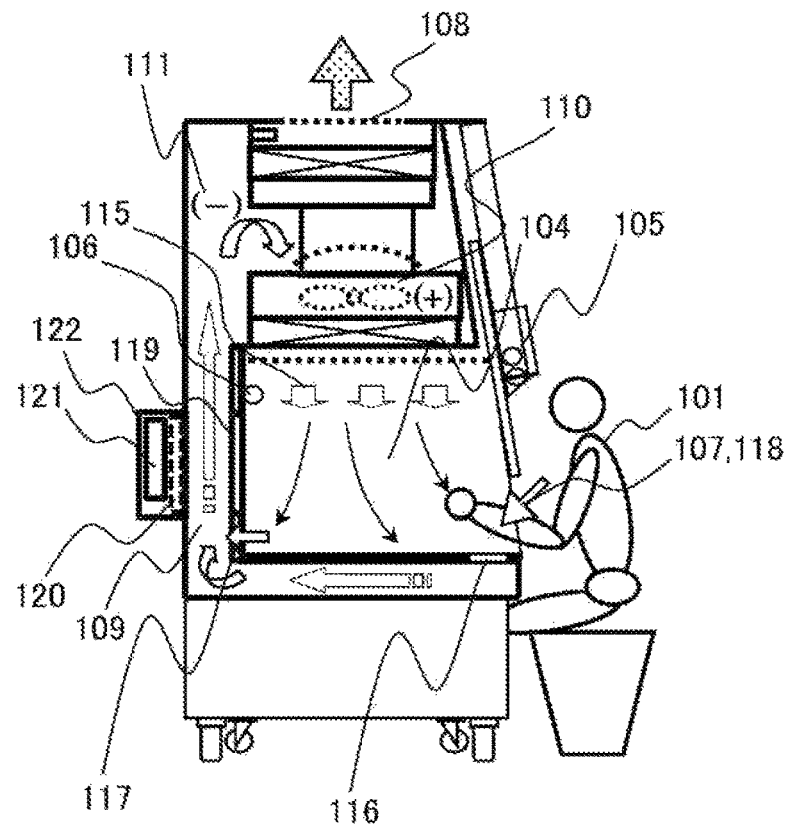
FIG. 1 is an example of a configuration diagram illustrating a cross-sectional side view of a safety cabinet according to a first embodiment.
Figure 2:
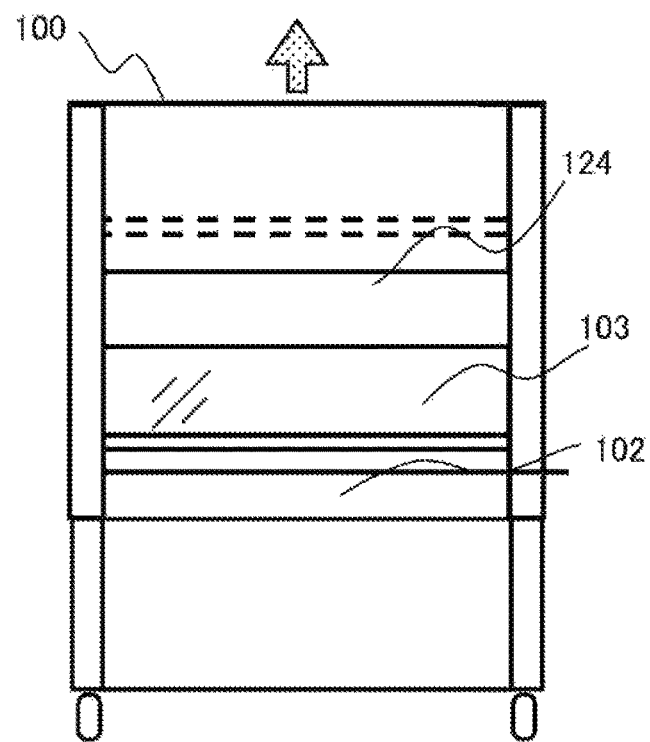
FIG. 2 is an example of an external front view of a safety cabinet according to the first embodiment.
Figure 3:
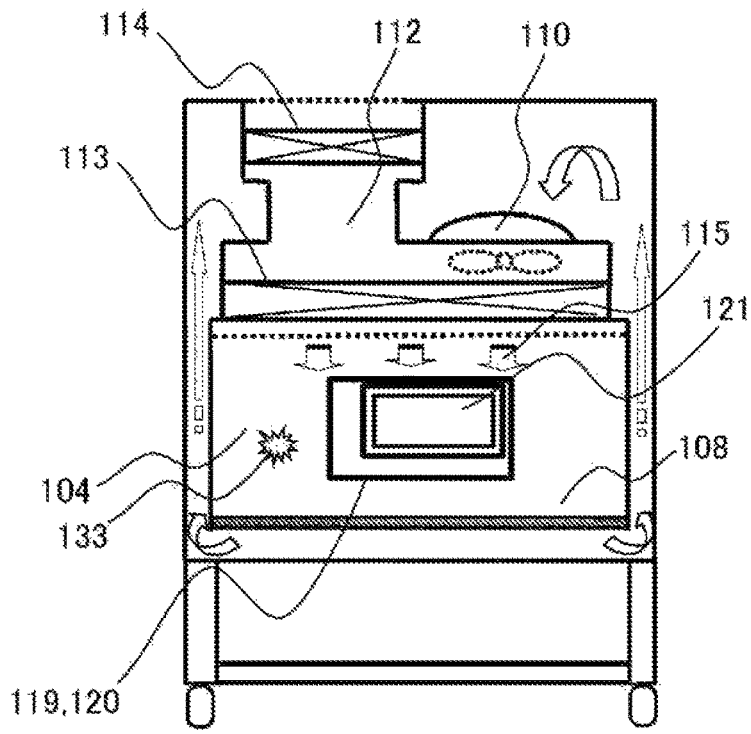
FIG. 3 is an example of a configuration diagram illustrating a cross-sectional front view of the safety cabinet according to the first embodiment.

FIGS. 1 through 3 are views illustrating a configuration example of a safety cabinet 100 corresponding to a Class II cabinet for biohazard countermeasure according to a first embodiment. FIG. 1 is an example of a configuration diagram illustrating a cross-sectional side view thereof, FIG. 2 is an external front view thereof, and FIG. 3 is an example of a configuration diagram illustrating a cross-sectional front view thereof.

An operator 101 inserts his/her arms through a front face opening 102 of the safety cabinet 100, and performs operation while looking through a front face shutter 103 into a work space 104. An illuminance suitable for operation is maintained in the work space 104 by an illuminating lamp 105. Further, a germicidal lamp 106 is generally provided at an upper portion on a back face of the work space 104. The germicidal lamp 106 is used auxiliary to sterilize an inner side of the work space 104 before and after operation, together with a decontamination operation of wiping using 70% alcohol, for example.

A general room air 107 sucked in through the front face opening 102 passes through a circulation flow path 109 composed of a lower portion of a work table 108 (lower face of the work space 104), a side face and a back face of the work space 104 and a body portion of the safety cabinet 100, and sucked into an air blower 110. This area where air having been contaminated (hereinafter referred to as "contaminated air") passes through to a suction side of the air blower 110 is called a negative pressure contamination plenum 111. The negative pressure contamination plenum 111 is a contaminated area where bacteria/virus 133 handled within the work space 104 may reach. The air sucked into the air blower 110 is pressurized in a pressure chamber 112, where a portion of the air is filtered by an HEPA filter for air supply 113 and supplied as cleaned air into the work space 104, and the other portion of the air is filtered by an HEPA filter for air discharge 114 and discharged outside the apparatus as cleaned air.

A blow-out air flow 115 supplied into the work space 104 cleans the inner side of the work space 104, and a portion of the air flow is sucked in through a front face suction slit 116 and another portion of the air flow is sucked in through a back face air suction port 117, which pass through the circulation flow path 109, and are sucked into the air blower 110.

An extremely important performance of the safety cabinet 100 is to prevent the operator from being infected by bacteria/virus 133 handled inside the safety cabinet 100, and this function is realized by isolating the air within the work space 104 from the air outside the safety cabinet 100 by an air isolation portion 118.

A transparent window within work chamber 119 is provided on a back face of the work space 104 to allow an operation to see through the back face, and a transparent window on back face of body 120 is provided on a back side of the transparent window within work chamber 119, which are separated by the circulation flow path 109. In other words, the transparent window adopts a double structure by the transparent window within work chamber 119 and the transparent window on back face of body 120, which allow the back face of the safety cabinet 100 to be viewed through the work space 104. The transparent window within work chamber 119 and the transparent window on back face of body 120 are formed by a material such as a tempered glass or a laminated glass. If a maintenance space cannot be provided on a back face of the safety cabinet 100, it is possible to arrange these transparent windows on a side face of the work space 104.

A display device (also referred to as display means) 121 such as a monitor screen is provided on a back face of the transparent window on back face of body 120. The display device 121 is fixed and protected by a monitor cover 122. Further, it is possible to arrange a notice board, an instruction book on which operation processes are described, or a display means displaying a construction schedule control chart or an operation manual in place of the display device 121, or objects can be directly adhered to the transparent window on back face of body 120.

If the monitor cover 122 is not attached, a configuration can be adopted where work contents and observe operations can be visually confirmed through the transparent windows on the back face of the body or the left or right side faces from the outer side of the body of the safety cabinet 100. In that case, the size (area) of the transparent window within work chamber 119 and the transparent window on back face of body 120 should be designed to have a wider area such that the confirmation of work contents or observation of operations can be facilitated, instead of designing the area to correspond to the size (area) of the display device 121.

As described, by providing the display device 121, the operator 101 can confirm SOP and sample data without interrupting the operation and without changing the work posture. Therefore, workability (reliability and efficiency of the work) can be improved.

Further, the operator can perform operations while confirming operation procedures and sample data through a display device such as a monitor screen provided at a position that does not cause diffused reflection, without interrupting the operation and without changing the work posture.

Since the display device such as the monitor screen is installed outside the contamination area, wiping (disinfection) and sterilization before and after operation or during change-over (when changing the sample being handled) becomes necessary. Thus, the operation efficiency is improved, and deterioration of the display device such as the monitor screen can be suppressed.

Further, adhesion of dirt to the transparent window formed of glass and the like arranged on a front face of the display means can be suppressed by forming an air flow that does not contact the transparent window.

The display device 121 is arranged in a general room outside the contaminated space such as the work space 104 and the negative pressure contamination plenum 111, such that the whole display device 121 is prevented from being in contact with contaminated air. Thereby, wiping (disinfection) and sterilization before and after the operation or during change-over (when changing the sample being handled) becomes unnecessary. Further, since the display device 121 is not arranged within the work space 104, it does not cause resistance in the flow path, such that a stable air flow is formed within the work space 104, and power consumption of the air blower and the like can be suppressed.

Further, even if sterilization of the whole work space 104 is performed using formaldehyde gas and the like to detoxify contaminants, since the display device 121 is not placed within the work space 104, there is no need to sterilize the display device 121, and failure of the device can be prevented.

Further, irradiation of UV-C waves as ultraviolet rays from the germicidal lamp 106 promotes deterioration of resin, whereas the transmission rate of UV-C waves through glass is approximately 0%. Therefore, if glass material is used for at least either the transparent window within work chamber 119 or the transparent window on back face of body 120 (though it is better to use the glass material for both windows), deterioration of the display device 121 such as the monitor screen caused by using the germicidal lamp 106 can be prevented.

In the present embodiment, it is not a necessary configuration to provide the display device (means) 121. That is, by providing the transparent window within work chamber 119 and the transparent window on back face of body 120, for example, an administrator of the operation can confirm the work content or the status of operation of the operator 101 from the back side of the safety cabinet 100.

The above-described configuration of the present embodiment has been described with reference to a safety cabinet, but it is also applicable to a cabinet ("Class I cabinet for biohazard countermeasure" according to Japanese Industrial Standard (WS)). In the present specification, the safety cabinets (Class II) and the Class I cabinets are generally referred to as "clean air apparatus". The present embodiment and other embodiments described hereafter are also applicable to cabinets for chemical hazard countermeasure. There are cases where the embodiments are applicable to Class III cabinets, but Class III cabinets are also included in the concept of the clean air apparatus.

[Second Embodiment]

The present embodiment is an example in which not only display by the display device 121 such as the monitor screen, but also monitoring from a remote monitor room (not shown) or conversation with the remote monitor room is enabled in the safety cabinet 100. According to the present embodiment, the safety cabinet 100 is used for description, similar to the first embodiment, but the embodiment can also be applied to a clean air apparatus.

Figure 4:
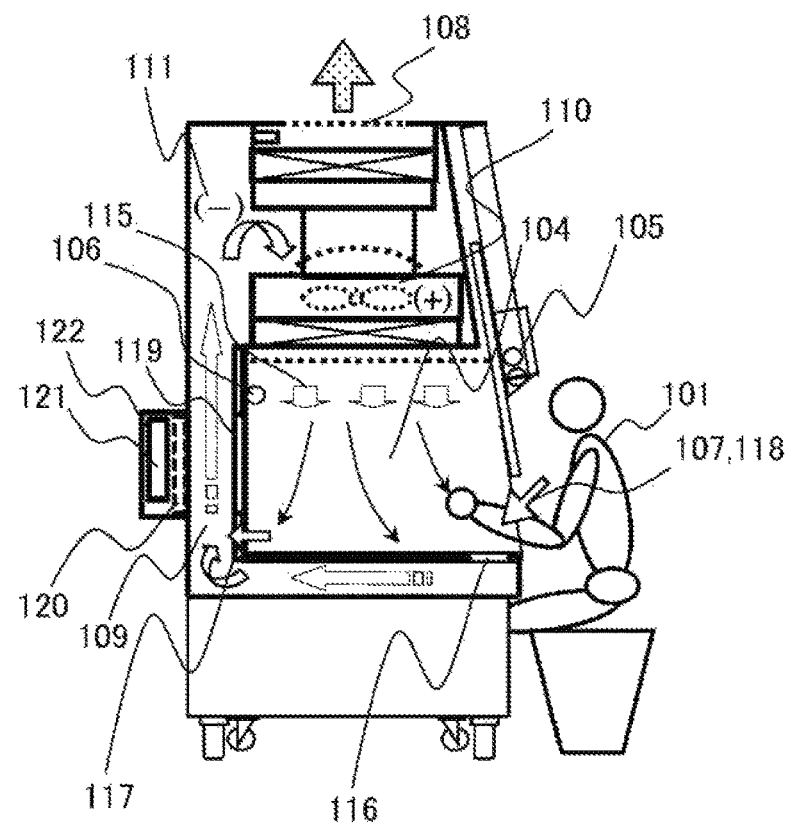
FIG. 4 is an example of a configuration diagram illustrating a cross-sectional side view of the safety cabinet according to a second embodiment.
Figure 5:
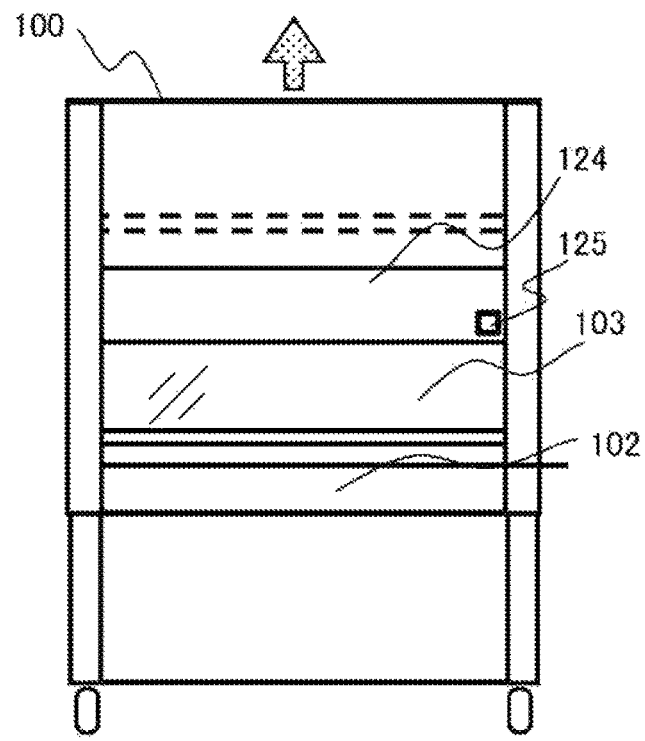
FIG. 5 is an example of an external front view of the safety cabinet according to the second embodiment.
Figure 6:
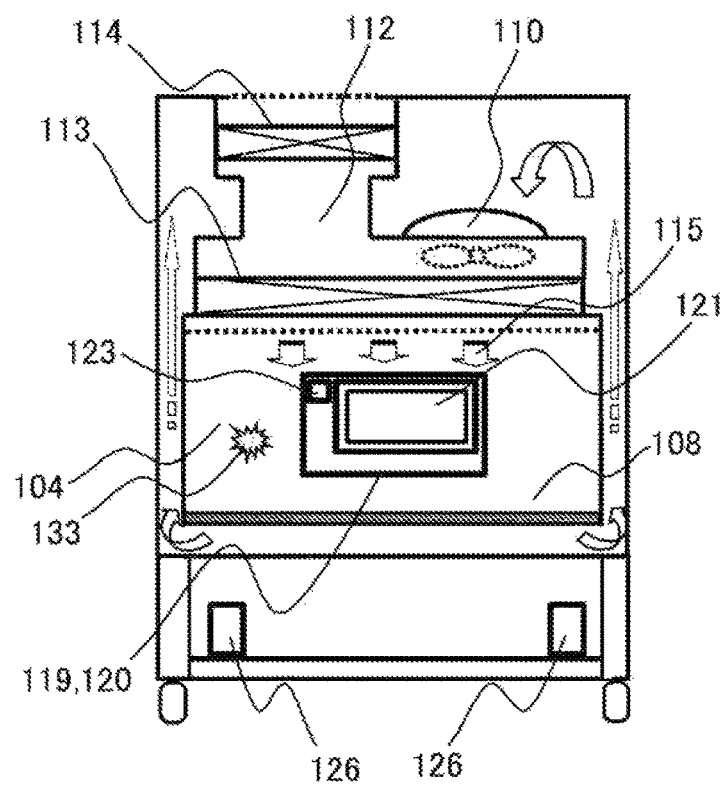
FIG. 6 is an example of a configuration diagram illustrating a cross-sectional front view of the safety cabinet according to the second embodiment.

FIGS. 4 through 6 illustrate a configuration example of a safety cabinet 100 corresponding to a Class II cabinet for biohazard countermeasure according to a second embodiment. FIG. 4 illustrates an example of a configuration diagram illustrating a cross-sectional side view thereof, FIG. 5 is an example of an external front view thereof, and FIG. 6 is an example of a configuration diagram illustrating a cross-sectional front view thereof.

In the configuration illustrated in FIGS. 4 through 6, the components denoted by the same reference numbers as those in FIGS. 1 through 3 and having the same functions will not be described.

Similar to the first embodiment, a display device 121 such as a monitor screen is provided on a back side of a transparent window on back face of the body 120 of a safety cabinet 100 of FIG. 4, but a network camera 123 is provided adjacent to the display device 121 within a monitor cover 122 covering the display device 121. An image of the work space 104 is taken through the camera from the back face side of the safety cabinet 100. Then, the video is displayed on the display device 121 such as the monitor screen, such that operation procedures, status of operation and condition of samples can be confirmed in real-time. Further, the video image can be sent to a remote monitor room for monitoring operation.

Further, a microphone 125 is provided on a decorative cover 124 storing an illuminating lamp 105, for example, and voice from an operator 101 (such as conversation with the remote monitor room) is entered through the microphone 125. An installation location of the microphone 125 is not restricted to the decorative cover 124, as long as the voice of the operator can be entered without interfering with the operation on an outer side portion of a body of the safety cabinet 100.

Furthermore, a speaker 126 is installed on a leg portion of the safety cabinet 100, for example, and voice instruction regarding the operation or a notification sound such as an alarm is output through the speaker 126. The installation location of the speaker 126 is not restricted to the leg portion, as long as output voice is intercepted without interfering with the operation on an outer side of the body portion of the safety cabinet 100.

Now, the display device 121 such as the monitor screen, the network camera 123, the microphone 125 and the speaker 126 (which may hereinafter be generally referred to as "peripheral equipment") are connected via a communication means such as a LAN with a control unit (both are not shown) disposed in the remote monitor room. Thereby, operation can be monitored from the remote monitor room, and the operator can communicate with an operator in the remote monitor room. The communication means can also be wireless.

The peripheral equipment is arranged on an outer side portion of the body of the safety cabinet 100 (that is, inside a general room) which is outside the contamination space such as the work space 104 and the negative pressure contamination plenum 111, so there is no need to decontaminate the peripheral equipment after the operation.

Further, even in a case where sterilization of the whole work space 104 is performed using formaldehyde gas to detoxify contaminants, there is no need to sterilize the peripheral equipment since they are not placed in the work space 104, such that failure is not caused.

Further, even with respect to irradiation of UV-C waves, which are ultraviolet rays output from the germicidal lamp 106, deterioration of peripheral equipment through use of sterilization lamps can be prevented, as described earlier, if glass material is used for at least either the transparent window within work chamber 119 or the transparent window on back face of body 120 (though it is better to use the glass material for both windows).

In the above description, an example of enabling monitoring to be performed also from a remote monitor room using the network camera 123, the microphone 125 and the speaker 126 as the peripheral equipment has been illustrated, but it is also possible to install the network camera 123 alone to the display device 121 as camera, and provide video images such as operation procedures, operation statuses and statuses of samples to the operator in a stand-alone manner. Thereby, the operator can confirm the state of the operation or the sample in real-time.

Further, the video image taken through the camera can be recorded if necessary for confirmation after operation.

[Third Embodiment]

The present embodiment illustrates an example in which dirt is prevented from being attached to the transparent window and maintenance operation is improved when a display device 121 such as a monitor screen disposed on a safety cabinet performs display.

Figure 7:
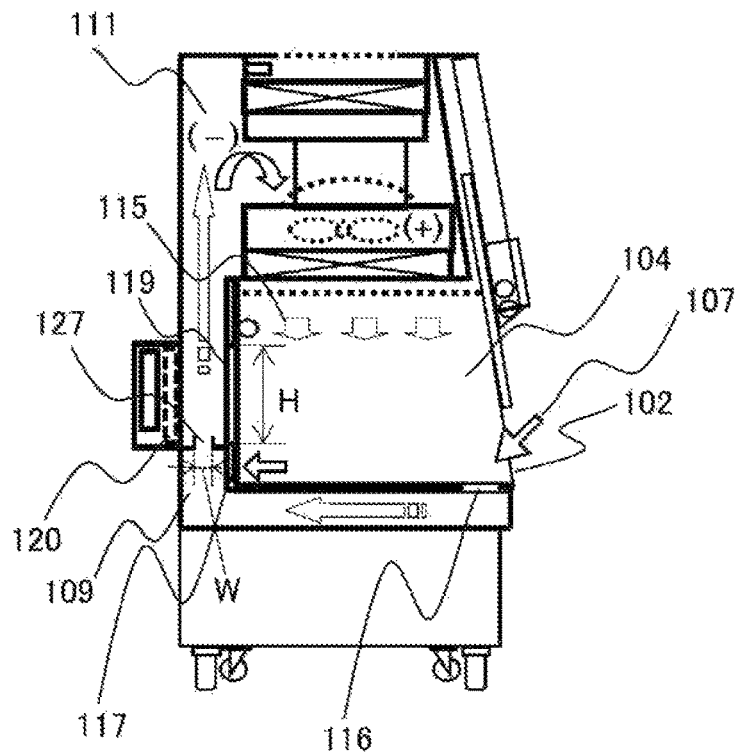
FIG. 7 is an example of a configuration diagram illustrating a cross-sectional side view of the safety cabinet according to a third embodiment.
Figure 8:
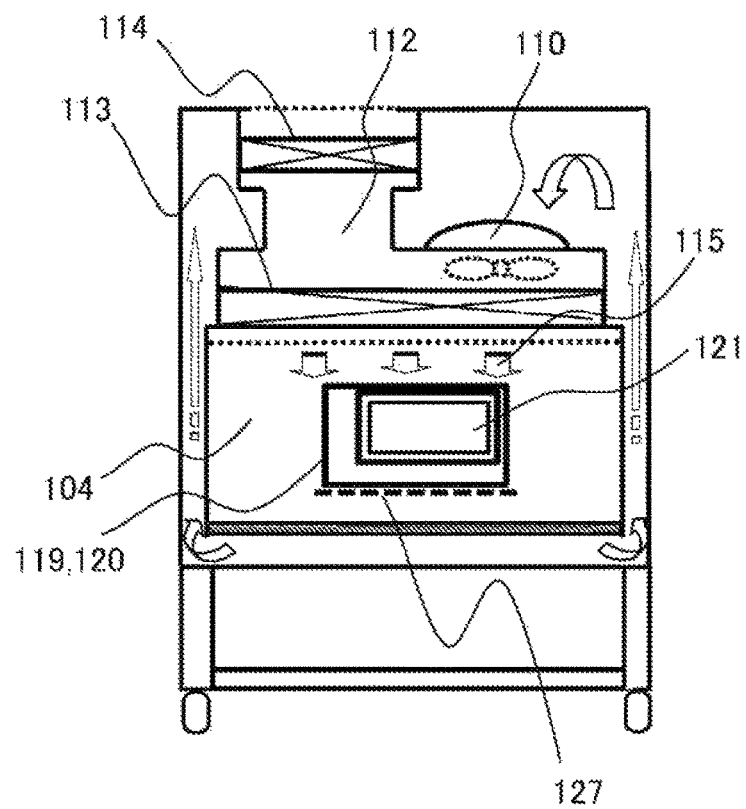
FIG. 8 is an example of an external front view of the safety cabinet according to the third embodiment.
Figure 9:
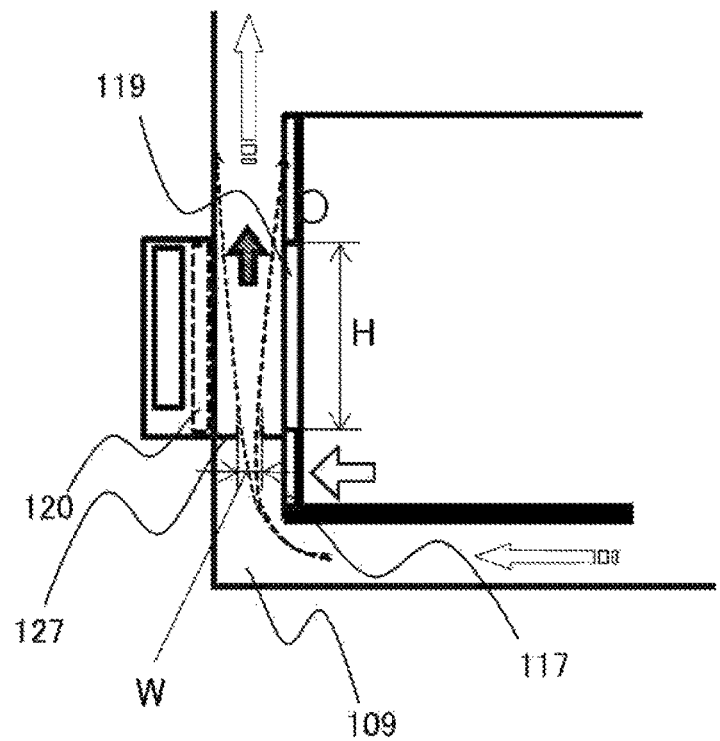
FIG. 9 is a view having enlarged a back side portion of a work chamber within a cross-sectional side structure of FIG. 7.

FIGS. 7 through 9 illustrate a configuration example of a safety cabinet 100 corresponding to a Class II cabinet for biohazard countermeasure according to a third embodiment. FIG. 7 is an example of a configuration diagram illustrating a cross-sectional side view thereof, and FIG. 8 is an example of an external front view thereof. FIG. 9 is a view having enlarged a back face portion within a work chamber according to the side cross-sectional structure of FIG. 7.

In the configuration illustrated in FIGS. 7 through 9, components assigned with the same reference numbers illustrated in FIGS. 1 through 3 and having the same functions are not described. The present embodiment is described using the safety cabinet 100, similar to the first and second embodiments, but it can also be applied to a clean air apparatus.

The blow-out air flow 115 sucked in through the front face opening 102 and supplied into the general room air 107 and the work space 104 is partially sucked in through the front face suction slit 116 and partially sucked in through the back face air suction port 117, and flows through the circulation flow path 109 formed on the back face of the work space 104.

A shielding plate 127 is provided on an inner side wall surface of the circulation flow path 109 at a portion immediately under the transparent window within work chamber 119 and immediately under the transparent window on back face of body 120. Thereby, dirt is prevented from being attached to the transparent window within work chamber 119 or the transparent window on back face of the body 120 from the contaminated air passing through the circulation flow path 109.

The shielding plate 127 is effective in preventing attachment of dirt within the contaminated air if the whole portion is shielded along a width direction of the transparent window portion, but if there is a large amount of circulated air, it becomes a resistance to the air flow of the circulation flow path 109, and it may case increase of consumption power of the air blower 110. In order to prevent this situation, as illustrated in FIGS. 7 and 9, a slit or an endpiece plate is provided at a center in a depth direction of the shielding plate 127. Therefore, as illustrated by a dotted line of FIG. 9, it becomes possible to prevent contaminated air from being in direct contact with the transparent window, while ensuring the airflow path. Further, as illustrated in FIG. 8, the width of the shielding plate 127 should at least be equal to the width of the transparent window within the work chamber 119 and the transparent window on back face of body 120.

A height of the transparent window is referred to as H, and a width of the slit or a width between the endpiece plates is referred to as W, wherein H and W are set to satisfy the following relationship.

$$W/H \geq 0.3$$

Thus, air flow of the circulation flow path 109 can configure an air flow that does not contact the transparent window directly.

Further, regarding a resistance within the apparatus, a resistance by change of speed of air flow discharged from the work space 104 and passing through the shielding plate 127 is determined to be within a range of 2 to 3 Pa by the characteristics of the air blower 110. According to such resistance, air can be discharged efficiently without the need to raise the performance of the air blower 110. If the resistance is too excessive, it is necessary to improve the performance of the air blower 110, and if the resistance is too small, it will not be possible to form an air flow that will not be in direct contact with the transparent window.

Now, regarding resistance within the apparatus, pressure loss is generated where velocity change occurs on the flow path, such that pressure loss $\Delta P$ generated by velocity change is represented by the following expression.

$$\Delta P = \eta \times (\tfrac{1}{2}) \times \rho \times (V1^2 - V2^2) \quad \text{(Expression 1)}$$

In (Expression 1), $\eta$ represents a pressure loss coefficient, $\rho$ represents fluid density ($\rho=1.2$ in the case of air), V1 represents flow velocity before change of velocity, and V2 represents flow velocity after change of velocity.

The pressure loss coefficient $\eta$ varies according to the material of the flow path, the fluid velocity and so on, but it will not exceed 1 in most cases, so it is allowable to use $\eta=1$ for a schematic calculation.

Next, regarding maintenance such as cleaning of the transparent window within work chamber 119 and the transparent window on back face of body 120, a configuration is adopted where the transparent window within work chamber 119 can be removed from the work space 104 and the transparent window on back face of body 120 can be removed from the outer side of the body of the safety cabinet 100. Thereby, both sides of the transparent window within work chamber 119 and the side of the transparent window on back face of body 120 facing the circulation flow path 109 can be cleaned. Furthermore, the configuration enabling the transparent window within work chamber 119 and the transparent window on back face of body 120 to be removed is effective for maintenance of the respective transparent windows even in a case where the shielding plate 127 according to the third embodiment is not provided.

[Fourth Embodiment]

The present embodiment illustrates an example of a method in which the operator utilizes the display device 121 such as the monitor screen to obey operation procedures and suppress operation losses.

Figure 10:
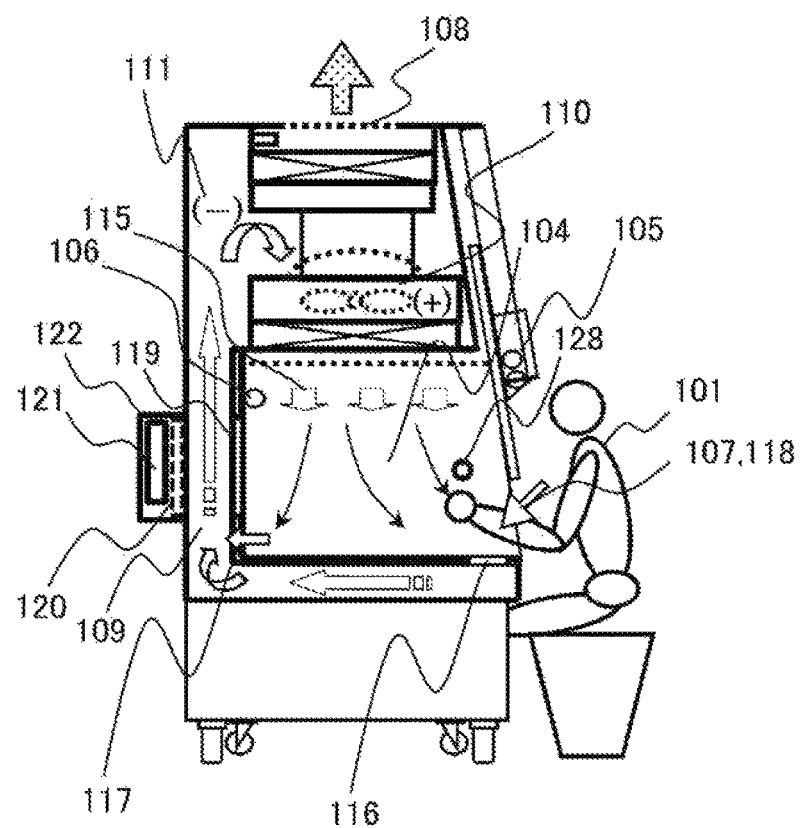
FIG. 10 is an example of a configuration diagram illustrating a cross-sectional side view of a safety cabinet according to a fourth embodiment.
Figure 11:
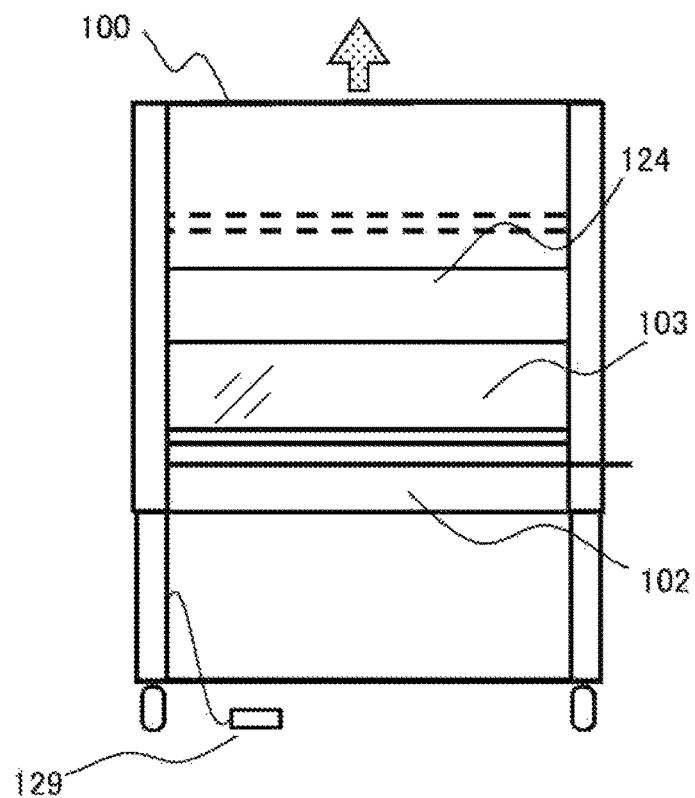
FIG. 11 is an example of an external front view of the safety cabinet according to the fourth embodiment.
Figure 12:
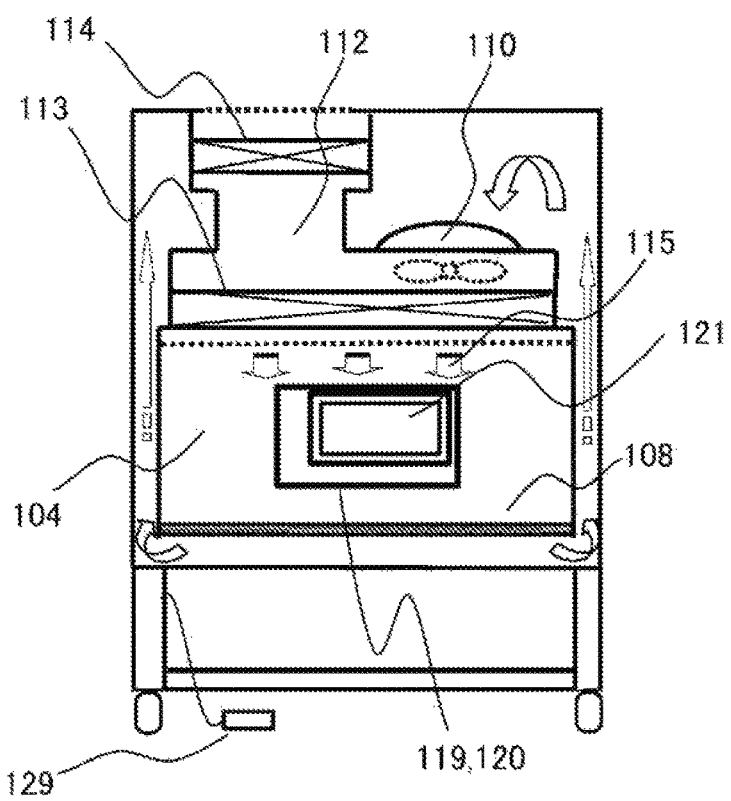
FIG. 12 is an example of a configuration diagram illustrating a cross-sectional front view of the safety cabinet according to the fourth embodiment.

FIGS. 10 through 12 are configuration examples of a safety cabinet 100 corresponding to a Class II cabinet for biohazard countermeasure according to a fourth embodiment. FIG. 10 is an example of a configuration diagram illustrating a cross-sectional side view thereof, FIG. 11 is an example of an external front view thereof, and FIG. 12 is an example of a configuration diagram illustrating a cross-sectional front view thereof.

As for the configurations illustrated in FIGS. 10 through 12, description of the components assigned with the same reference numbers as those illustrated in FIGS. 1 through 3 and having similar functions are omitted. The present embodiment is described using the safety cabinet 100, similar to the first embodiment, but it can also be applied to a clean air apparatus.

In a state where an operator 101 confirms an SOP or a sample data, the information is displayed on a display device 121 such as a monitor screen. The operator 101 looks at the contents of the display on the screen, and if the work content or the like being displayed is completed, he/she presses a button switch 128 disposed within a work chamber of the safety cabinet 100, or operates a foot switch 129 disposed on a floor of the body portion of the safety cabinet 100 by foot. Thereby, a notice notifying that the displayed work content has been completed is sent to a control unit (not shown) provided in the safety cabinet 100 or a control unit (not shown) provided in a remote monitor room.

Then, a display screen of the display device 121 such as the monitor screen is switched via a control unit having received notice of the completion signal, and a subsequent operation process can be performed. If the completion signal is not notified, the display screen will not be switched and the subsequent operation cannot be performed.

As described, if the operator performs a confirmation operation for each operation procedure, the operation can be performed along a predetermined operation procedure without any risk of omission of operation, and further, the current operation process can be confirmed from the remote monitor room.

Further, the display device 121 such as the monitor screen can be equipped with a function to display the whole operation process. In that case, the operator can confirm the positional relationship of the current operation within the whole procedure.

Moreover, if a video image of a model operation prepared in advance is displayed on the display device 121 such as the monitor screen, the operation can be performed while confirming operation procedures in an even more facilitated manner.

Even further, operation can be confirmed using an input apparatus equipped with a function of a microphone or a camera disposed according to the second embodiment. For example, in a state where the operator has completed the operation displayed on the display device 121 such as the monitor screen, if voice output such as "starting next operation" or "process A has been completed" is detected through a microphone, it becomes possible to recognize the completion of the displayed operation. Moreover, the completion of the displayed operation can also be recognized by detecting a direction of a visual line of the operator using the camera. The completion of the operation can also be detected simply by arranging a switch not shown on the floor or within a cleaned space, and operating the switch. These methods are collectively referred to as input means.

The method for transiting to a subsequent operation has been illustrated above, but it is also possible to enable the display screen to be returned for confirmation of the work content. In that case, for example, input of voice such as "return to previous operation" or input of detection of a specific visual operation using a camera can be utilized. In addition, operation using an independently arranged switch or operation of pressing a switch twice in a row can be utilized, if switch input is selected. In that case, it is possible to not only move the screen of the work content forward but also to rewind the screen, and the operator can confirm, for example, that no error had been performed during the operation. Further, a function to display the whole operation process can be provided. The operator can comprehend the positional relationship of the current operation process within the whole process.

[Fifth Embodiment]

The present embodiment illustrates an example of a method utilizing a display device 121 such as a monitor screen or a speaker 126, and informing an error in a case where necessary cleanliness within a work space cannot be maintained.

Figure 13:
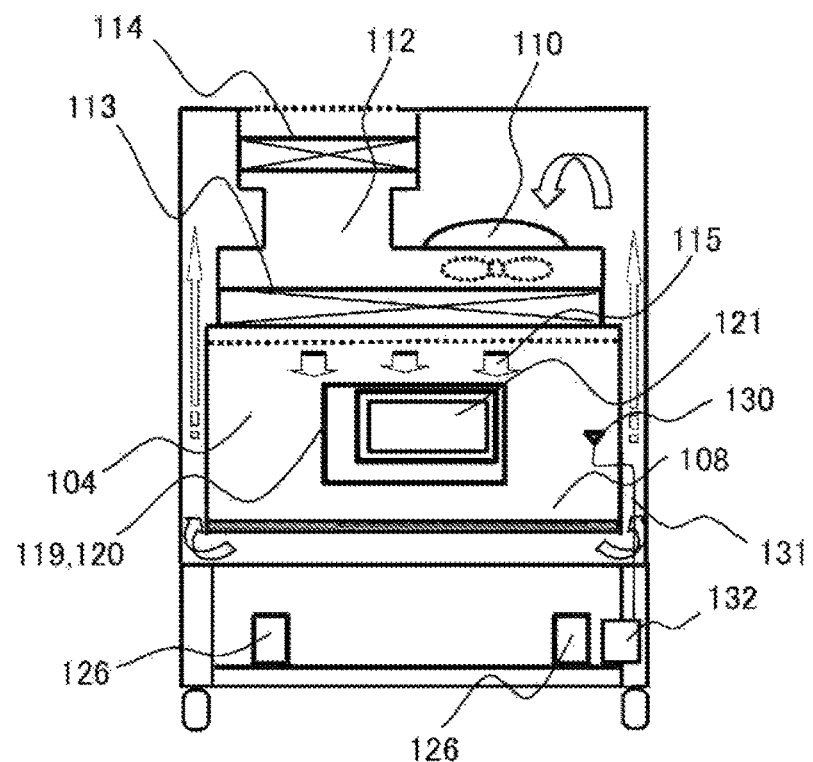
FIG. 13 is an example of a configuration diagram illustrating a cross-sectional front view of a safety cabinet according to a fifth embodiment.

FIG. 13 illustrates an example of a configuration diagram illustrating a cross-sectional front view of a safety cabinet corresponding to a Class II cabinet for biohazard countermeasure according to a fifth embodiment. The configuration diagrams illustrating a cross-sectional side view and an external front view of the safety cabinet 100 are basically similar to those of the second embodiment, so they will not be described, and only the different configurations will be described. The present embodiment will be described using the safety cabinet 100, similar to the other embodiments, but it can also be applied to a clean air apparatus.

Dust within a work space 104 is measured using, as a general dust measuring device, a light scattering air-borne particle counter (particle counter) or a relative densitometer (photometer). According to ISO (International Organization for Standardization), cleanliness of air is represented by the number of dusts contained in a unit volume, such that in many cases, a light scattering air-borne particle counter (particle counter) counting the number of dusts is used as the measuring device.

FIG. 13 illustrates an example where dust within the work chamber is measured using the light scattering air-borne particle counter (particle counter). The air within the work space 104 is connected to a particle suction port 130, and a fixed amount of air per unit time is taken via a sampling tube 131 into the light scattering air-borne particle counter (particle counter) 132. The dust contained in the taken-in air can be counted and accumulated to a predetermined air quantity, to thereby count the number of dust contained in a unit volume.

At this time, in a state where the work space 104 cannot maintain a necessary cleanliness for a predetermined operation, a warning output from a particle counter 132 is used to perform at least either a monitor output on the display device 121 such as the monitor screen or a voice output to the speaker 126. At least either a color output of the display of the display device 121 such as the monitor screen or the voice output from the speaker 126, and in the case of color, lighting or blinking of a red light, can be used to notify abnormality of cleanliness.

As described, in a case where the cleanliness within the work space cannot be maintained due, for example, to a source generating dust exists within the work space, a warning can be output to trigger improvement of operation. Finally, it leads to prevention of contamination of samples.

Furthermore, if the number of dust detected by the particle counter 132 is displayed on the display means serving as the display device 121 such as the monitor screen, a numerical value can be displayed in addition to the warning. Furthermore, a temperature and humidity within the work space can be displayed on the display device 121. In these cases, the condition of internal environment can be confirmed by numerical values, and not just based on the state of warning. The number of dust, the temperature, the humidity and the like as information within the work space are collectively referred to as internal environment information within work space.

[Sixth Embodiment]

Figure 14:
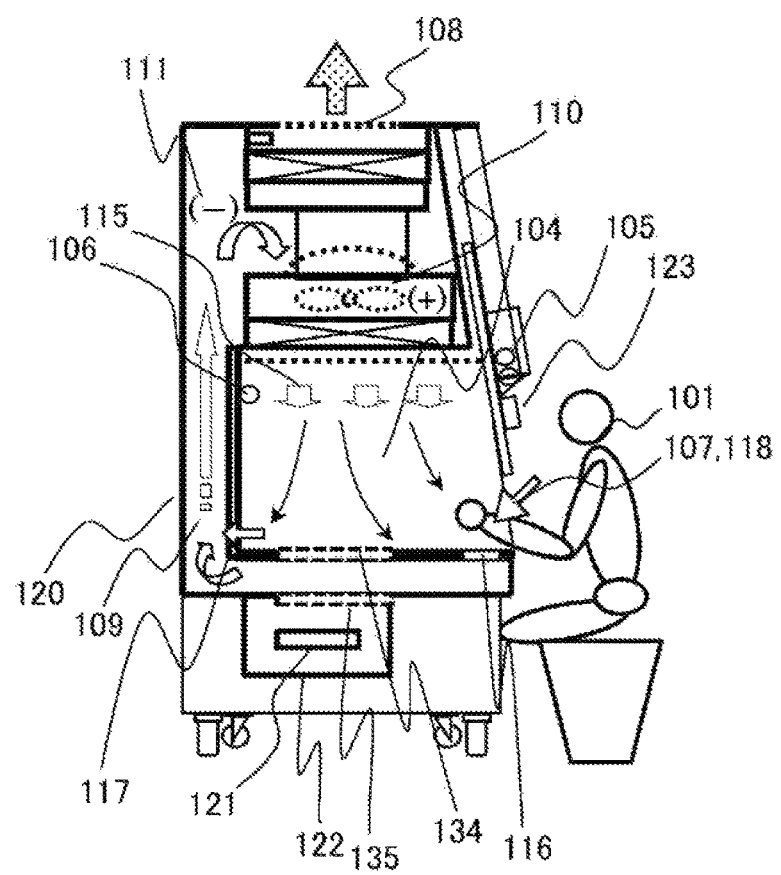
FIG. 14 is an example of a configuration diagram illustrating a cross-sectional side view of a safety cabinet according to a sixth embodiment.

A sixth embodiment will be described with reference to FIG. 14. The numerical reference numbers that are used in the first through fifth embodiments are not described, and only the configurations that differ will be described. A safety cabinet 100 is used in describing the present embodiment, similar to other embodiments, but it can also be applied to a clean air apparatus.

The sixth embodiment relates to a configuration in which a display device (display means) 121 such as a monitor, a typical example of which is a liquid crystal display, is arranged in a space below a work table. In order for the light generated from the display device 121 to reach an operator, a transparent window on lower face of work table 134 and a transparent window on lower face of body 135 are provided with a circulation flow path 109 arranged therebetween. Further, a monitor cover 122 fixing the display device 121 is provided. The shape of the monitor cover 122 is not restricted to the covering structure as illustrated, and can be modified as long as the cover enables to fix the display device 121.

In other words, work schedule, operations, and internal environment information within work space described in the fifth embodiment displayed on the display device 121 are transmitted through the transparent window on lower face of body 135 serving as a first transmission member, transmitted through the circulation flow path 109, transmitted through the transparent window on lower face of work table 134 provided on the work table serving as a second transmission member, and passed through the front face shutter 103 to reach the operator 101.

Information displayed on the display device 121 is displayed through input means described in other embodiments. The inner side of the work chamber can be observed by installing a network camera 123 on the front face shutter 103. In observing the work space, it is possible to associate information on a petri dish or a test tube being arranged with the operation information, and display the petri dish or the test tube to be subjected to subsequent operation. Operational errors of the operator can be reduced by adopting this configuration.

[Seventh Embodiment]

Figure 15:
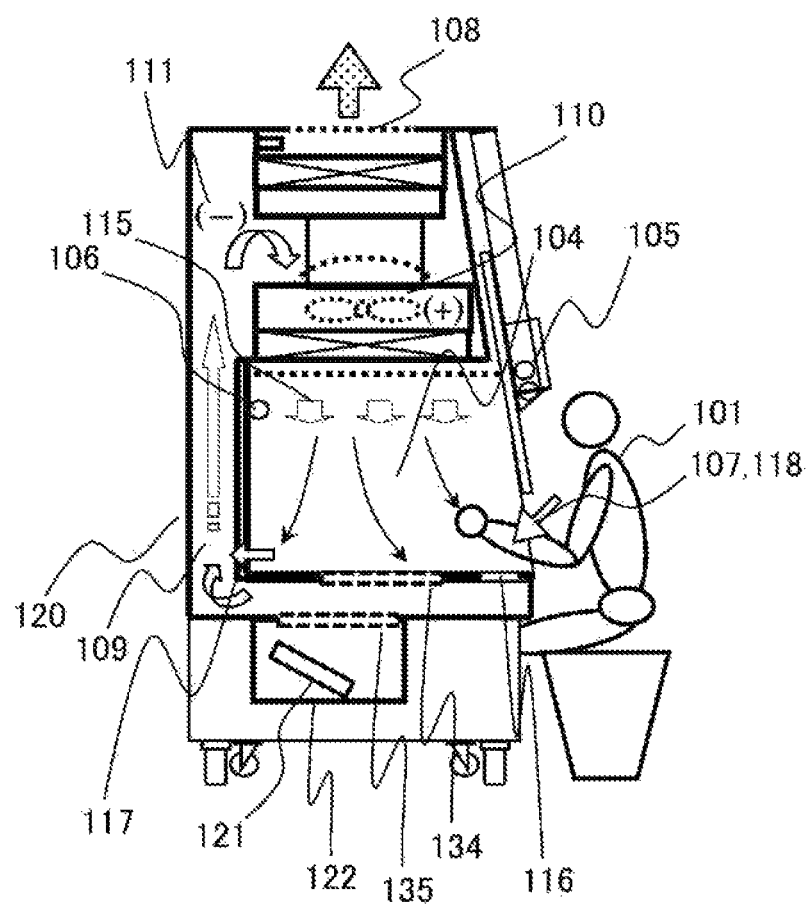
FIG. 15 is an example of a configuration diagram illustrating a cross-sectional side view of a safety cabinet according to a seventh embodiment.

A seventh embodiment will be described with reference to FIG. 15. The description on components denoted by reference numbers of the first to sixth embodiments are omitted, and only the configuration that differs therefrom will be described. The present embodiment is described using a safety cabinet 100, similar to other embodiments, but it can also be applied to a clean air apparatus.

The seventh embodiment relates to a configuration where a display device (display means) 121 such as a monitor, a typical example of which is a liquid crystal display, is arranged in a space below a work table, similar to the sixth embodiment, but the difference from the sixth embodiment is that the display device 121 is tilted and forms an angle with a horizontal plane, and that a positional relationship between a transparent window on lower face of work table 134 and a transparent window on lower face of body 135 differ. That is, a display surface of the display device 121 faces the operator 101. The shape of a monitor cover 122 can be modified, as long as it fixes the display device 121. Similar to the sixth embodiment, the cover 122 is not required to adopt a configuration to cover the display device 121.

Information related to an internal environment information within work space or a work schedule as described in the fifth embodiment is displayed on the display device 121. The information displayed on the display device 121 is output toward a direction of a front face shutter 103, transmitted through a transparent window on lower face of body 135 serving as a first transmission member, transmitted through a circulation flow path 109, transmitted through a transparent window on lower face of work table 134 disposed on a work table serving as a second transmission member, and transmitted through the front face shutter 103 to reach the operator 101.

The transparent window on lower face of body 135 and the transparent window on lower face of work table 134 are disposed substantially in parallel via a circulation flow path 109.

In other words, the display device 121 is tilted with an angle from the horizontal plane, and arranged so that a plane of a display area of the display device 121 is arranged toward the operator 101. Then, assuming that the plane of the display area of the display device 121 is extended toward the operator, the transparent window on lower face of body 135 serving as a first transmission member is provided at an area where the extended plane intersects with a lower face of the body. Further, the transparent window on lower face of work table 134 serving as a second transmission member is provided at an area where the plane extended further toward the operator intersects with the lower face of the work table. That is, the transparent window on lower face of work table 134 and the transparent window on lower face of body 135 are provided within the space composed of the operator 101 and the display device 121.

In other words, the transparent window on lower face of work table 134 and the transparent window on lower face of body 135 are provided in an area where the operator can visibly confirm the display area of the display device 121.

According to this configuration, a visibility of a display means 121 from the operator 101 can be improved even further than the sixth embodiment. Moreover, if a liquid crystal display is used as the display device 121, a viewing angle can be ensured.

Moreover, it is also possible to adopt a configuration of the transparent window on lower face of work table 134 and the transparent window on lower face of body 135 to transmit a part of the area of the display device 121, instead of all the area of the display device 121.

The first to seventh embodiments have been described above, but clearly, the configuration of the first embodiment is the basis of the present invention, and the second, fourth and fifth embodiments can be combined arbitrarily. Further, the third embodiment can clearly be applied to (combined with) the second, fourth or fifth embodiment, or to a combination of second, fourth and fifth embodiments. It is also possible to combine necessary configurations with the sixth and seventh embodiments.

In any arrangement, the air flow of the circulation flow path 109 can be ensured. Further, the operator 101 can confirm the display device 121 displaying work schedules and the like via the transparent window on back face of body 120 or the transparent window on lower face of body 134.

REFERENCE SIGNS LIST

100 safety cabinet, 101 operator, 102 front side opening, 103 front face shutter, 104 work space, 105 illuminating lamp, 106 germicidal lamp, 107 general room air, 108 work table, 109 circulation flow path, 110 air blower, 111 negative pressure contamination plenum, 112 pressure chamber, 113 HEPA filter for air supply, 114 HEPA filter for air discharge, 115 blow-out air flow, 116 front face suction slit, 117 back face air suction port, 118 air isolation portion, 119 transparent window within work chamber, 120 transparent window on back face of body, 121 display device (monitor screen), 122 monitor cover, 123 network camera, 124 decorative cover, 125 microphone, 126 speaker, 127 shielding plate, 128 button switch, 129 foot switch, 130 particle suction port, 131 sampling tube, 132 particle counter, 133 bacteria/virus, 134 transparent window on lower face of work table, 135 transparent window on lower face of body

The invention claimed is:

1. A clean air apparatus at least comprising:
   a work space formed on an inner side of a front face shutter and configured to maintain a state of negative pressure; and
   a circulation flow path formed of a lower face side of the work space, a side face side of the work space, a back face side of the work space, and an outer side portion of a body of the apparatus, and configured to discharge air flowing into the work space,
   wherein transparent windows are respectively provided on a portion of a back wall or a side wall of the work space and on a portion of a rear wall or a side wall of the body of the clean air apparatus separated by the circulation flow path from the back wall or the side wall of the work space, and an operator can see through both walls via the transparent windows wherein a display device is place on an outer side portion of the transparent window provided on the portion of the rear wall or the side wall of the body of the clean air apparatus, such that the display apparatus can be seen through the front face shutter.

2. The clean air apparatus according to claim 1, wherein at least one of the transparent windows is formed of a glass material.

3. The clean air apparatus according to claim 1, wherein an imaging device is provided adjacent to the display device.

4. The clean air apparatus according to claim 1, wherein a voice input device or a voice output device is provided.

5. The clean air apparatus according to claim 1, wherein if a completion notice of a work content displayed on the display device is entered, a screen indicating a next operation process is switched and displayed.

6. The clean air apparatus according to claim 4, wherein if it is detected based on a dust measurement within the work space that a cleanliness required in the work space is not maintained, at least one of the display device and the voice output device is used to inform abnormality of the cleanliness by at least either a display color or a voice output, and if color is used, either by lighting or blinking the color display.

7. The clean air apparatus according to claim 1, wherein immediately below the respective transparent windows at an inner side wall of the circulation flow path, a slit having a predetermined width or an endpiece plate separated by the predetermined width is provided at a center in a depth direction, and a shielding plate having a length at least corresponding to a width of the transparent window is provided.

8. The clean air apparatus according to claim 1, wherein the transparent window provided at a portion of a back wall or a side wall of the work space is configured to be removable from the work space side, and the transparent window provided at a portion of a rear wall or a side wall of the body of the clean air apparatus is configured to be removable from the outer side of the body of the clean air apparatus.

9. A clean air apparatus comprising:

a work space comprising a work table;

a supply system configured to supply cleaned air to the work space through a first air cleaning means by an air blowing means;

a front face shutter formed on a front face of the work space;

a work opening connected to a work space on a lower portion of the front face shutter;

a discharge system configured to take in air from the work opening and discharge air via a second air cleaning means to an outer side of the apparatus; and a pressure chamber connected to the first air cleaning means, the second air cleaning means and the air blowing means, wherein a flow path for contaminated air is provided between the work opening and the second air cleaning means, the flow path for contaminated air is separated from the work space by a first partition wall arranged adjacent to the work space, and further separated by a second partition wall opposed to the work space and arranged adjacent to outer air, and transparent windows are provided on the second partition wall and the first partition wall wherein a display means is provided on the second partition wall, and information displayed on the display means transmitted through the transparent window, such that the display apparatus can be seen through the front face shutter.

10. The clean air apparatus according to claim 9, wherein the transparent window is formed of glass.

11. The clean air apparatus according to claim 9, wherein the display means displays a work content to be performed by an operator.

12. The clean air apparatus according to claim 9, further comprising an input means provided to determine a state of an operator.

13. The clean air apparatus according to claim 12, wherein if information indicating completion of operation performed by an operator displayed on the display means is entered from the input means, the display means displays a work content that differs from the operation to be performed by the operator displayed on the display means.

* * * * *